United States Patent [19]

Rouge

[11] Patent Number: 4,501,150
[45] Date of Patent: Feb. 26, 1985

[54] ACOUSTIC POLARIMETER

[75] Inventor: Jean Rouge, Paris, France

[73] Assignee: Thomson-CSF, Paris, France

[21] Appl. No.: 482,193

[22] Filed: Apr. 5, 1983

[30] Foreign Application Priority Data

Apr. 6, 1982 [FR] France .................. 82 05966

[51] Int. Cl.³ ............................................ G01N 29/00
[52] U.S. Cl. ........................................ 73/628; 73/645
[58] Field of Search .................. 73/628, 645, 625, 642

[56] References Cited

U.S. PATENT DOCUMENTS 3,587,297  9/1968  Kammer ...................... 73/597
4,138,894  2/1979  Robert et al. ................. 73/625

FOREIGN PATENT DOCUMENTS 2295633  7/1976  France .
2333231  6/1977  France .
2069697  8/1981  United Kingdom .

*Primary Examiner*—Anthony V. Ciarlante

*Attorney, Agent, or Firm*—Oblon, Fisher, Spivak, McClelland & Maier

[57] ABSTRACT

An acoustic polarimeter is provided for measuring the acoustic birefringence of a plate with parallel faces.

The plate to be measured is fixed to one face of an acoustically isotropic body and to the other face are fixed transducers having their linear transfer axis at 90° from each other transmitting waves at pulsation $\omega$ modulated respectively by $\cos \Omega t$ and $\sin \Omega t$. After reflection from the rear face of the sample, the signals $X_1$ and $Y_1$ received by the transducers are processed in processing circuits. The signals $x_1$ and $y_1$ are multiplied by a signal $\cos(\omega t + \phi)$ supplied by a phase-shifter controlled by a signal $S_1$. After filtering, signals $X$ and $Y$ are obtained which are used for generating two signals $A$ and $B$. A microprocessor receiving the amplitudes of these signals $A$ and $B$ controls the phase-shifter and supplies the birefringence angle $\phi$. The direction of the first axis is obtained by synchronous detection of signal $A_1$ by $\sin 2\Omega t$.

2 Claims, 1 Drawing Figure

U.S. Patent Feb. 26, 1985 4,501,150
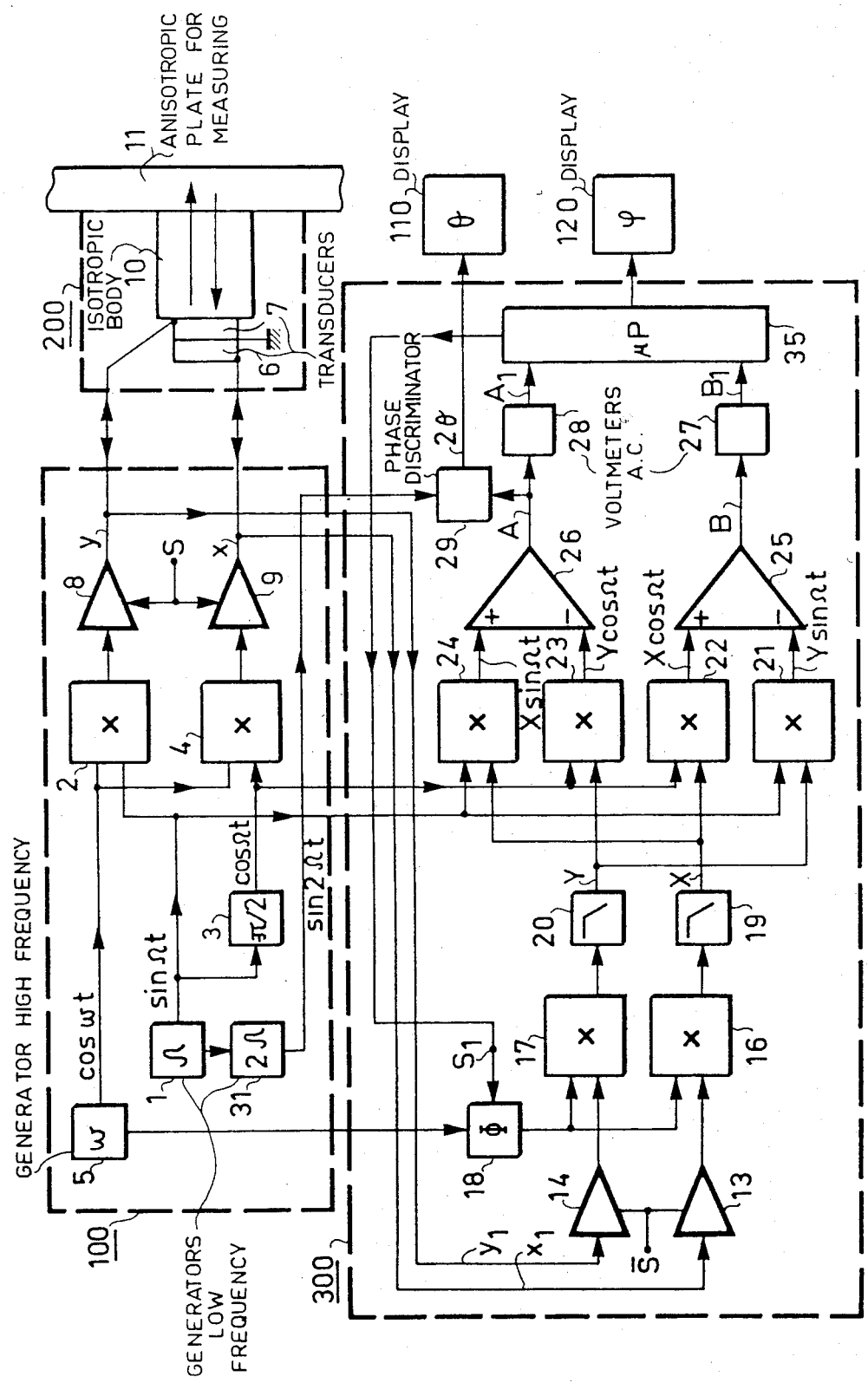

ACOUSTIC POLARIMETER

BACKGROUND OF THE INVENTION

The present invention relates to an acoustic polarimeter for determining the acoustic birefringence of a solid with parallel faces, for one direction of the acoustic wave perpendicular to the parallel faces.

The method of analyzing stresses by optical birefringence induced in a transparent solid is currently used under the name of "photoelasticimetry" or measurement of photoelasticity. This method may be transposed to non transparent solids such as metals with acousto-elasticimetry based on the acoustic birefringence of the solids.

Acoustic birefringence is the consequence of the elastic anisotropy presented by most solids, whether it is structural in origin or induced by stresses or the two combined. As in optics, this acoustic birefringence is characterized by two main slow and fast axes perpendicular to the direction of propagation and related to the speed of the transverse acoustic waves polarized parallel to these axes. Two parameters are sufficient for determining it: the orientation $\theta$ of the fast axis with respect to a reference direction and the phase-shift $\phi$ between the slow and fast waves after passing through the solid.

It is known from U.S. Pat. No. 4,138,894 to determine the parameters $\phi$ and $\theta$ of a plate with parallel faces by disposing two transducers close to the input face of this plate, the transducers transmitting or receiving waves polarized at 90° with respect to each other at the angular frequency $\omega$. The transmitted waves are modulated at a so-called low frequency angular frequency $\Omega$, so as to obtain a polarization outputted by the assembly of the two transducers which rotates at the angular frequency $\Omega$. The signals received by the two transducers are processed in circuits which also receive the signals at the angular frequency $\omega$ shifted in phase by $\phi$ by a manual phase-shifter. By adjusting this phase-shifter the value of $\phi$ may be obtained by display, $\theta$ being obtained by synchronous detection of a signal at the angular frequency $\Omega$.

The device has the disadvantage of requiring adjustment of the phase-shifter to a predetermined value which requires accurate calibration. Moreover, the value of $\phi$ is not obtained directly.

The polarimeter of the invention has the advantage with respect to the prior art of supplying directly without adjustment of $\phi$ the parameters $\phi$ and $\theta$ and it thus facilitates use of acousto-elasticimetry in mechanics, whereas the known methods could only be applied in specialized laboratories.

According to the main feature of the invention, this is an acoustic polarimeter for determining the birefringence parameters $\theta$ and $\phi$ of a plate with parallel faces, this plate being fixed to the endmost face of an elongated isotropic body with parallel faces, formed from a material propagating acoustic waves of frequency $\omega/2\pi$ while on the other endmost face of this body is placed a pair of transducers having their linear transverse axes of polarization at 90° with respect to each other, the electric signals applied to the first and second transducers being respectively of the form $\cos \Omega t \cos \omega t$ and $\sin \Omega t \cos \omega t$, where $\Omega/2\pi$ is a low frequency ($\Omega << \omega$), signals $x_1$ and $y_1$ being received by the two transducers after reflection from the rear face of the birefringent plate and these signals being multiplied by the signal $\cos (\omega t - \phi)$ supplied by a phase-shifter, these signals processed and filtered supplying the signals X and Y; wherein the signals X and Y are both multiplied by $\cos \Omega t$ and $\sin \Omega t$ and a differential amplifier supplies the alternating signal A such that $A = X \sin \Omega t - Y \cos \Omega t$ and a second differential amplifier supplies the alternating signal B so that: $B = X \cos \Omega t - Y \sin \Omega t$ measured respectively by AC voltmeters and wherein means allow, by acting successively on the phase-shifter, signals A and B to be cancelled out and so signal $A_B$, value of the amplitude of A, $A_1$ for $B=0$ and signal $B_A$, value of the amplitude of $B_1$ for $A=0$ to be obtained and wherein $\phi$ is determined from these values by the relationship $\tan \phi = A_B/B_A$, $\theta$ being obtained by a phasemeter receiving the signal A and a signal $\sin 2\Omega t$.

BRIEF DESCRIPTION OF THE DRAWINGS

Other features and advantages of the invention will become clear from the following description, illustrated by the drawing in which:

FIG. 1 gives the complete block diagram of the acoustic polarimeter of the invention. It may be subdivided into three main parts: the transmitter 100, the measuring head to be fixed on the sample 200 and the processing unit 300.

DESCRIPTION OF THE PREFERRED EMBODIMENT

The role of the transmitter is to transmit into the sample through the measuring head a linearly polarized transverse acoustic wave, of high frequency pulsation $\omega$ and whose direction of polarization rotates at the angular rate $\Omega$. By way of non limiting example, the high frequency of the acoustic wave may be chosen at 2 MHz and the frequency related to the rotation pulsation $\Omega$ at 70 Hz.

The oscillator 1 of pulsation $\Omega$ feeds a $\sin \Omega t$ voltage to the input of the multiplier circuit 2 and, through phase-shifter 3, a $\cos \Omega t$ voltage to a multiplier input 4. By way of example, these two voltages in quadrature may be obtained from a bistable oscillator delivering a square signal of quadruple frequency to logic circuits, which deliver two square signals in quadrature at the required frequency. By filtering the harmonics, the two sinusoidal signals in quadrature are obtained.

The other inputs of the multiplier circuits 2 and 4 are driven by a high frequency $\cos \omega t$ voltage coming from oscillator 5. The multiplication operation carried out in circuits 2 and 4 gives for one in channel x an $E \cos \Omega t \cos \omega$ signal and in channel y an $E \sin \Omega t \cos \omega t$ signal. These two signals are transmitted to the measuring head through amplifiers 8 and 9.

The measuring head is formed of body 10, made from a material capable of transmitting the transverse acoustic waves without attenuation and without modifying the polarisation. This material must then be elastically isotropic. This may be advantageously an amorphous body such as glass or vitreous silica, but metals or plastic materials may be suitable, if they fulfil the conditions of elastic isotropy and low attenuation. This body 10 has two flat parallel faces one of which is bonded to the sample 11, whose elastic anisotropy parameters $\theta$ and $\phi$ it is desired to measure. Thin film bonding of body 10 to sample 11 ensures good transmission of the transverse acoustic waves.

Two transducers 6 and 7, vibrating in shearing fashion, are bonded to the other face of body 10. Generally made from piezoelectric ceramic, these transducers may be made from a magnetostrictive material or be Y cut quartzes. They are oriented so that their axes of polarization are crossed at 90° one from the other. They may be bonded side by side to the face of body 10 but it is preferably to superimpose them so that the acoustic paths are propagated along a common axis in body 10 and sample 11. Transducers 6 is driven by the voltage of channel x and transducer 7 by that of channel y which must be slightly delayed by the travel time in 7 so that the transmitted waves come into phase in body 10. The combination in 10 of these two waves transmitted by channels x and y gives a transverse wave with rectilinear polarization rotating at the angular rate $\Omega$. It is propagated in 10 then in sample 11 where it is reflected from the opposite face to return to the transducers 6 and 7. To avoid standing waves, the transmission is pulsed by means of a disabling voltage S applied to amplifiers 8 and 9. One of the functions of body 10 is to serve an acoustic delay line so that the wave reflected by the rear face of 11 only reaches transducers 6 and 7 after the end of the transmission pulse. Electric signals $x_1$ and $y_1$ generated by these transducers are transmitted to the processing circuit 300.

In the processing part 300, the signals from channels $x_1$ and $y_1$ are transmitted to one of the two inputs of multipliers 16 and 17 through amplifiers 13 and 14. A voltage S disables these amplifiers for the period of the transmission pulses. The other inputs of multipliers 16 and 17 are driven by a $\cos(\omega t + \phi)$ voltage, delivered by oscillator 5 through phase-shifter 18, which produces the phase-shift $\phi$ by control from a signal $S_1$. These multipliers provide synchronous detection, which is followed by filtering in filters 19 and 20, so as to eliminate the high frequency components of the resulting signals X and Y.

Two multiplier groups 21, 22, 23 and 24 receive, on the one hand, the signals X and Y and, on the other hand, $\sin \Omega t$ and $\cos \Omega t$ voltages in quadrature available in the transmitter part 100. A differential amplifier 25 works out the difference B between the $\cos \Omega t$ signal X coming from multiplier 22 and the $\sin \Omega t$ Y signal coming from 21. Similarly, the difference A is provided by a differential amplifier 26 between X. $\sin \Omega t$ and Y. $\cos \Omega t$ supplied by multipliers 24 and 23.

The alternating signal A is applied to a phasemeter 29 which also receives the reference signal proportional to $\sin 2\Omega t$. The output signal from the phasemeter provides the value $2\theta$, the value of $\theta$ being displayed on an indicator 110.

The alternating signals A and B at the angular frequency $\Omega$ are applied to AC voltmeters 27 and 28, which supply the digitalized values of the amplitudes $A_1$ and $B_1$ of these signals to a microprocessor 35. At the output of the microprocessor the digital value of $\phi$ is obtained, which is displayed on indicator 120.

The operation of the microprocessor is the following. It generates the signal $S_1$ for controlling the phase shift of phase-shifter 18. Electronic control phase-shifters are well known. For a particular value of $\phi$, the value of $A_1$ is zero and at this zero crossing of $A_1$, the corresponding value $B_A$ of $B_1$ is stored. Similarly, for another particular value of $\phi$ $B_1$ is cancelled out and at this zero crossing of $B_1$ the corresponding value of $A_1$, $A_B$ is stored in another memory.

In a first operating cycle, the microprocessor determines the value $B_A$, in a second cycle it determines the value $A_B$ and in a third cycle it uses the stored values to work out the calculation of $\phi$, which is given by:

$\phi = \arctan(A_B/B_A)$

This value of $\phi$ is displayed on indicator 120.

An acoustic polarimeter has been described which supplies the phase-shift angles and the direction of the neutral axes by direct display.

What is claimed is:

1. An acoustic polarimeter for determining the birefringence parameters $\theta$ and $\phi$ of a plate with parallel faces comprising:
    an elongated body of isotropic material having parallel end faces made from a meterial propogating acoustic waves of the frequency $\omega 2\pi$;
    a means for fixing said plate to one of the end most faces of said elongated isotropic body;
    a pair of transducers having their linear transfers axis of polarization at 90° from each other placed at the other end face of said elongated body of isotropic material;
    a means for applying electrical signals to said first and second transducers being respectively of the form $\cos \Omega t \cos \omega t$ and $\sin \Omega t \cos \omega t$, where $\Omega/2\pi$ is of a low frequency ($\Omega << \omega$);
    means for receiving through said transducers the signals $x_1$ and $y_1$ reflected from the rear face of said birefrigent plate;
    a first phase shifter supplying the signal $\cos(\omega t + \phi)$;
    multiplying means for multiplying said signals $x_1$ and $y_1$ by the signal produced by said phase shifter;
    processing and filtering means for providing signals X and Y wherein said signals X and Y are both multiplied by the signals $\cos \Omega t$ and $\sin \Omega t$;
    differential amplifier means supplying an alternate signal A such that $A = X \cos \Omega t - Y \sin \Omega t$;
    second differential amplifier means supplying the alternate signal B such that $B = X \cos \Omega t - Y \sin \Omega t$;
    a phase meter and display for obtaining $\phi$ from signal A and a signal $\sin 2\Omega t$;
    two ac voltmeter means for receiving said alternating signals A and B at the alternating frequency $\Omega$;
    means for supplying digitalized values of amplitude $A_1$ and $B_1$;
    second phase shift means;
    means for generating a signal $s_1$ for controlling said second phase shift means;
    means for computing the zero crossing of said signals being provided to said second phase shift means;
    first memory means for storing the value of $B_1$ at the point at which the zero crossing of signal $A_1$ occurs;
    second memory means for storing the signal $A_1$ at the point at which $B_1$ has its zero crossing;
    means for computing $\phi$ based on the formula of arc tan (value stored in said second memory means/value stored in said first memory means);
    display means for displaying the value of $\phi$.

2. The polarimeter as claimed in claim 1, wherein the digitalized signals of $A_1$ and $B_1$ supplied by the AC volt-meters are applied to a microprocessor which controls by a signal $S_1$ the phase-shift produced by the phase-shifter and wherein in this microprocessor are stored successively the values of $A_B$ and $B_A$ (Amplitudes of signals A and B respectively), and these stored values are then read out for calculating the value of $\phi$.

* * * * *